(12) United States Patent
Park et al.

(10) Patent No.: US 8,329,106 B2
(45) Date of Patent: Dec. 11, 2012

(54) MINIATURIZED APPARATUS FOR REAL-TIME MONITORING

(75) Inventors: Han Oh Park, Daejeon (KR); Hanee Park, Daejeon (KR); Jong Soo Baek, Daejeon (KR)

(73) Assignee: Bioneer Corporation, Daejeon (KR)

( * ) Notice: Subject to any disclaimer, the term of this patent is extended or adjusted under 35 U.S.C. 154(b) by 313 days.

(21) Appl. No.: 11/661,410

(22) PCT Filed: Sep. 1, 2005

(86) PCT No.: PCT/KR2005/002899
§ 371 (c)(1),
(2), (4) Date: Feb. 28, 2007

(87) PCT Pub. No.: WO2006/025703
PCT Pub. Date: Mar. 9, 2006

(65) Prior Publication Data
US 2008/0032416 A1     Feb. 7, 2008

(30) Foreign Application Priority Data
Sep. 2, 2004   (KR) .................. 10-2004-0069866

(51) Int. Cl.
*G01N 21/64* (2006.01)
*B01J 19/00* (2006.01)

(52) U.S. Cl. .............. 422/82.08; 436/172; 422/129; 422/130; 250/201.5

(58) Field of Classification Search ............... 422/82.08, 422/129, 130; 436/172; 250/201.5
See application file for complete search history.

(56) References Cited

U.S. PATENT DOCUMENTS

| | | | |
|---|---|---|---|
| 5,475,210 A | * | 12/1995 | Taguchi et al. ............... 250/205 |
| 5,720,923 A | | 2/1998 | Haff et al. |
| 5,779,977 A | * | 7/1998 | Haff et al. ..................... 422/68.1 |

OTHER PUBLICATIONS

PArk et al. Cylindrical Compact Thermal-Cycling Device for Continuous-Flow Polymerase Chain Reaction.Analytical Chemistry. (2003) 75:6029-6033.*
Made-in-China.com: http://www.made-in-china.com/showroom/edytian/product-detailPbeQYUHrVgkR/China-Photocatalyst-Cold-Cathode-Germicidal-UV-Lamp-Linear-Type-.html.*

* cited by examiner

*Primary Examiner* — Krishnan S Menon
*Assistant Examiner* — Rebecca M Fritchman
(74) *Attorney, Agent, or Firm* — Nath, Goldberg & Meyer; Jerald L. Meyer; Stanley N. Protigal

(57) ABSTRACT

The present invention relates to a apparatus for quantitative continuous real-time monitoring to monitor a continuous reaction of biochemical reagent and the reaction, such as DNA. More particularly, the present invention is directed to a miniaturized apparatus for real-time monitoring of biochemical reaction, which comprises capillary tubes (100) wherein biochemical reaction mixture flow; a thermal conduction block (120) which is coiled with capillary tube several rounds in order and composed of several blocks for temperature control of which temperatures are different from each other for heating or cooling the biochemical reaction mixture which flow in capillary tube, and a temperature controller which controls the temperature of above temperature control block; a radiation part (130) to radiate the reaction mixture flowing through the capillary tube and a light receiving section (140) which receives and measures the intensity of the fluorescence generated from the capillary tubes.

10 Claims, 5 Drawing Sheets

[Fig. 1]
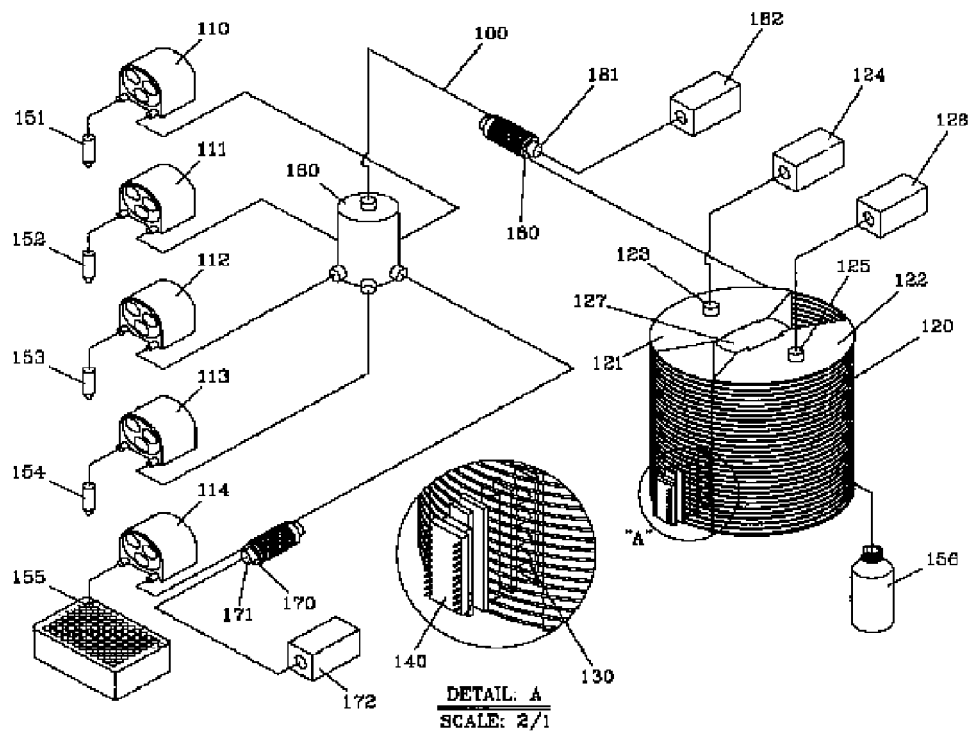
[Fig. 2]
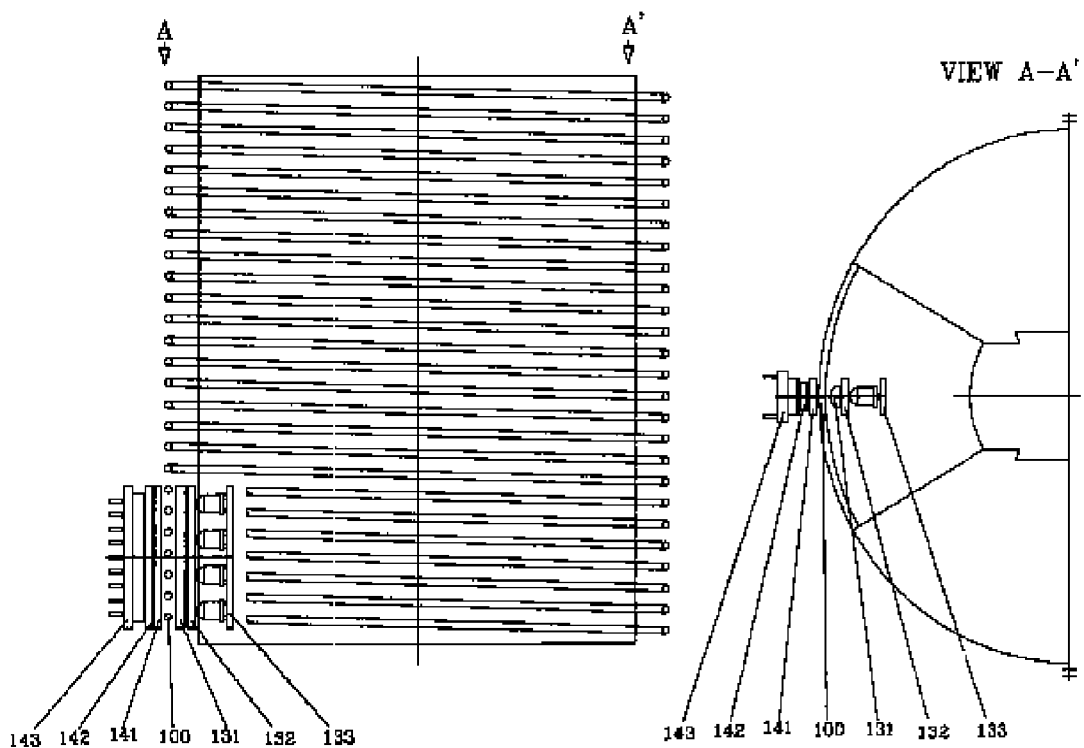

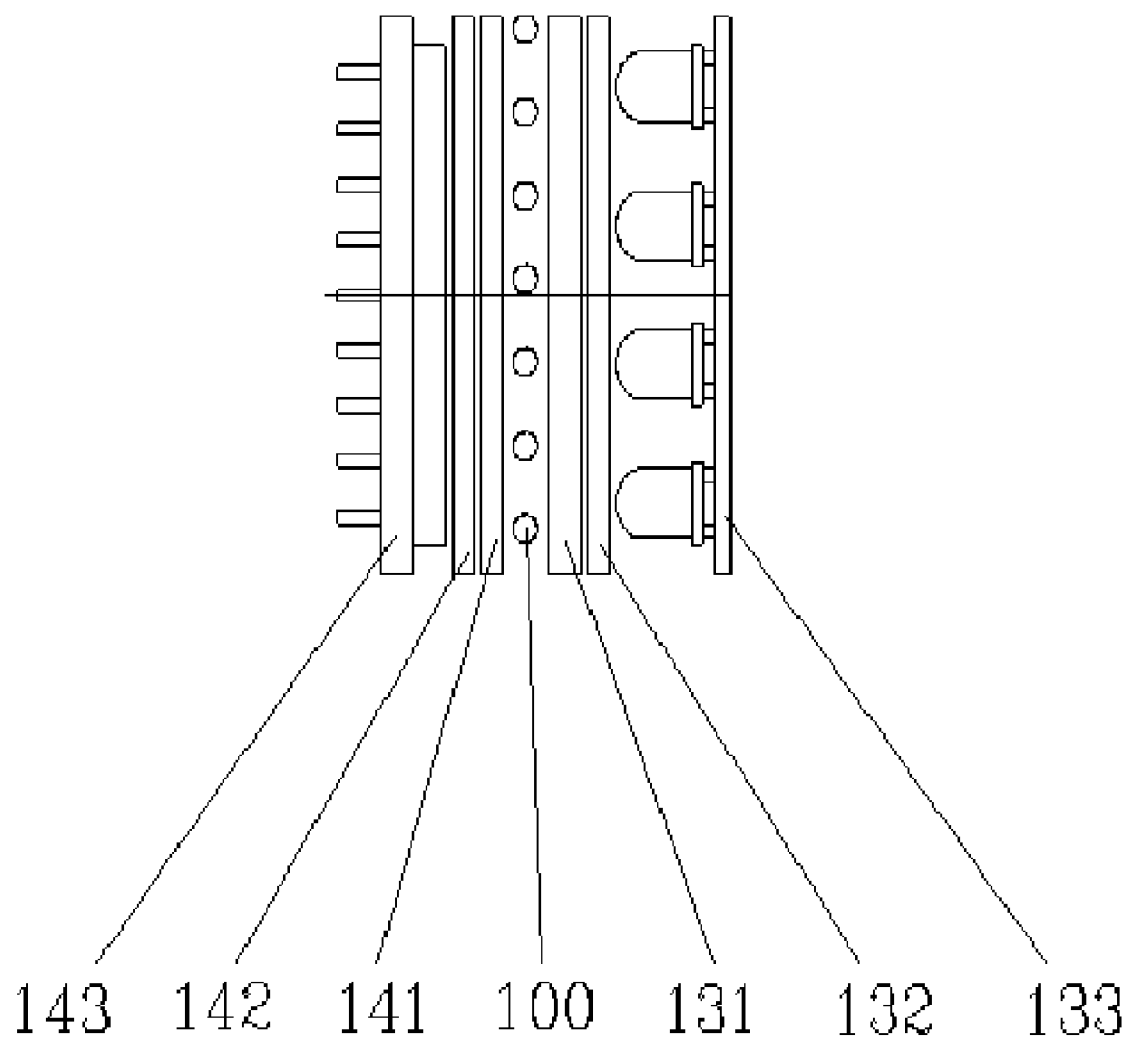
[Fig. 3]
143  142  141  100  131  132  133

[Fig. 4]
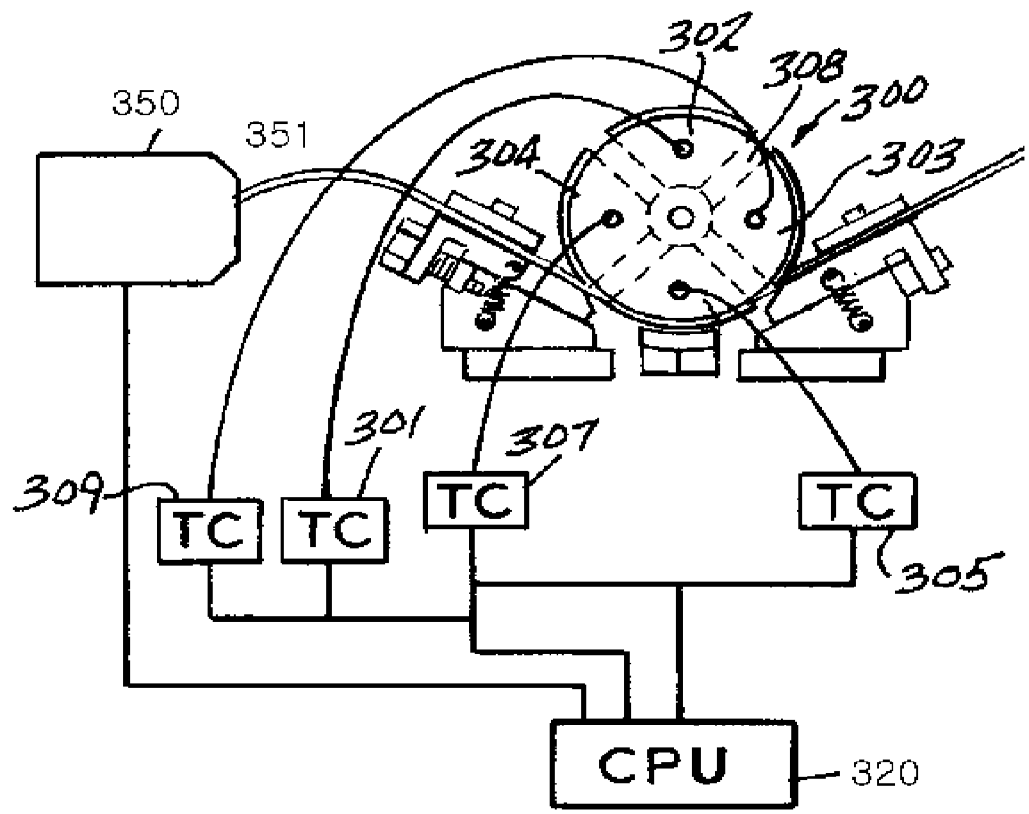
[Fig. 5]
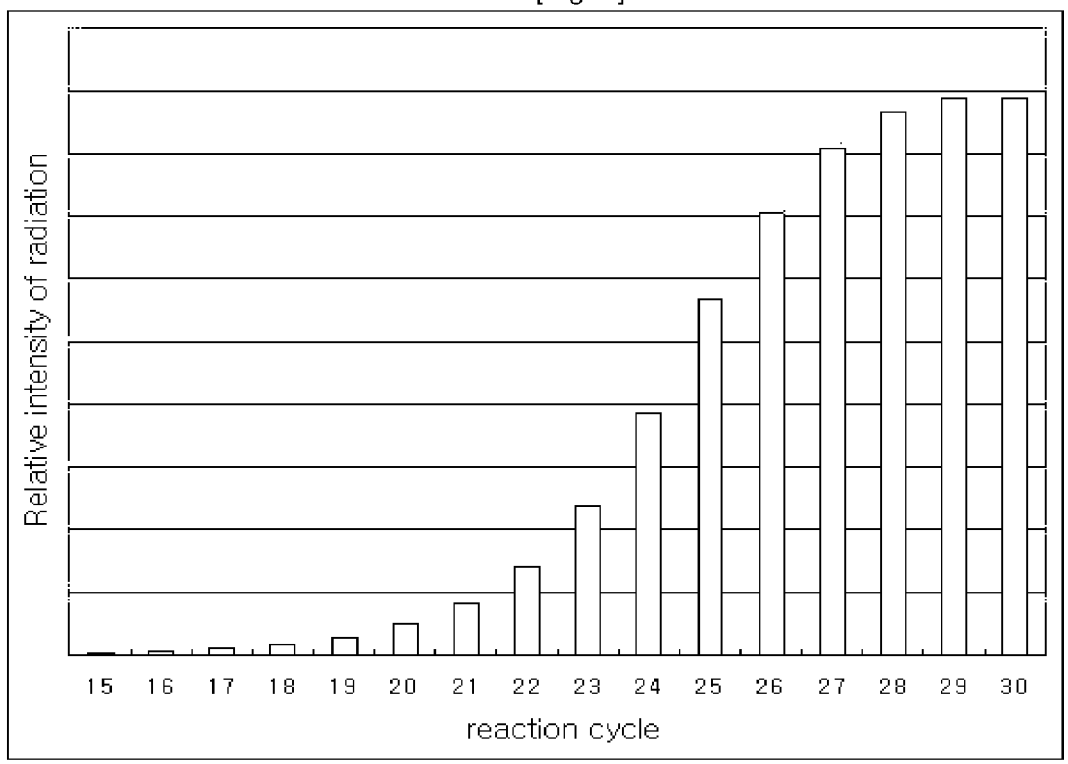

[Fig. 6]
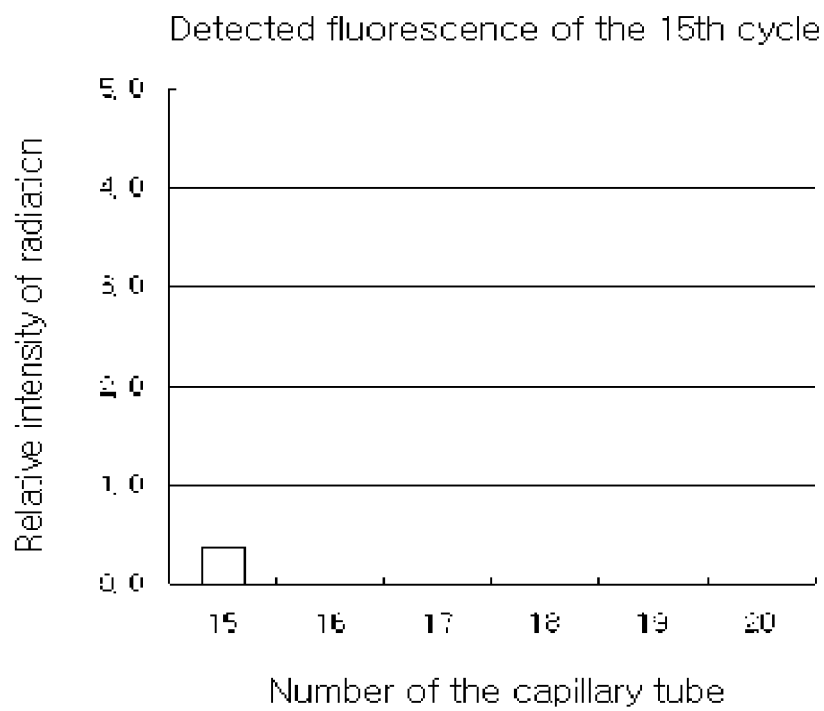
[Fig. 7]
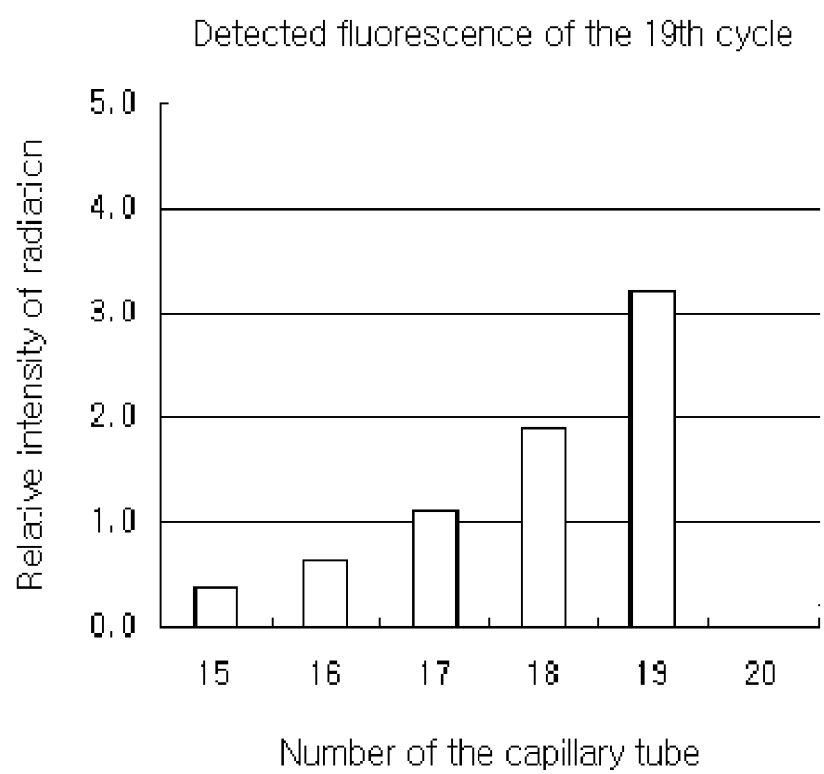

[Fig. 8]
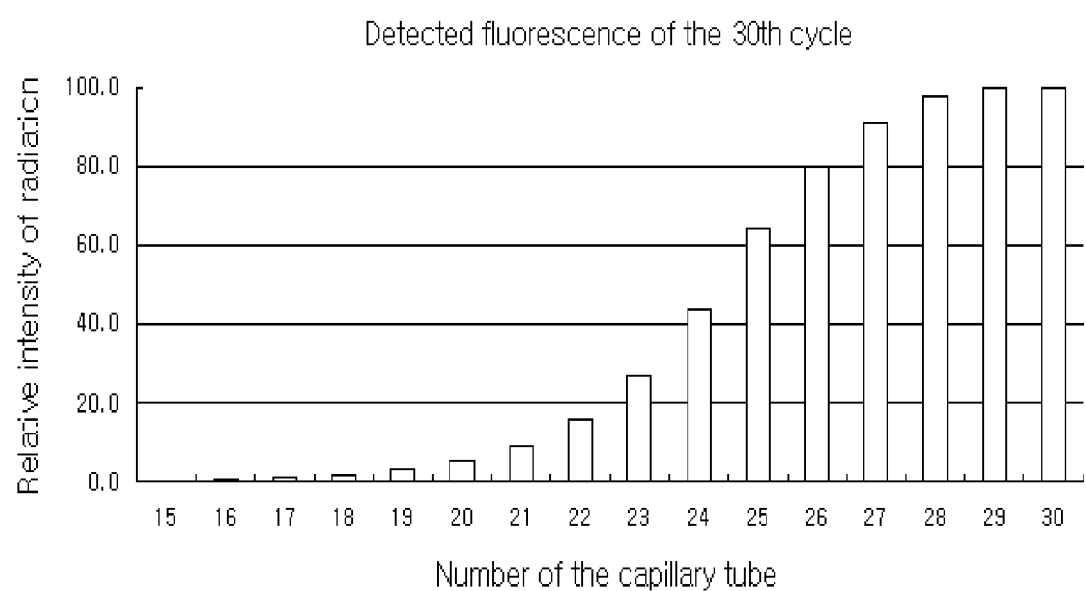

MINIATURIZED APPARATUS FOR REAL-TIME MONITORING

TECHNICAL FIELD

The present invention relates to a continuous real-time quantitative monitoring apparatus to monitor a continuous reaction of biochemical reagent and the reaction product thereof, such as DNA. More particularly, the present invention is directed to a miniaturized apparatus for real-time monitoring of biochemical reaction, which comprises capillary tubes (100) wherein the biochemical reaction mixture flow; a thermal conduction block (120) which is coiled with capillary tube several rounds in order and composed of several blocks for temperature control of which temperatures are different from each other for heating or cooling the biochemical reaction mixture which flow in capillary tube, and a temperature controller which controls the temperature of above temperature control block; a radiation part (130) to radiate the reaction mixture flowing through the capillary tube and a light receiving section (140) which receives and measures the intensity of the fluorescence generated from the capillary tubes.

BACKGROUND ART

The Polymerase Chain Reaction (PCR) is a process to amplify DNA by replicating a certain part of DNA repeatedly, which produces identical DNA in large amount from an infinitesimal amount of DNA.

Through the Polymerase Chain Reaction, it is possible to selectively amplify a desired part of DNA collected from huge DNA like genome DNA. The Polymerase Chain Reaction comprises 3 steps as follows.

1) DNA Denaturation

Double-stranded DNA (dsDNA) is separated into single-stranded DNA (ssDNA) by heating DNA at between 90° C. to 96° C. Though the double-stranded DNA (dsDNA) can be denatured to single-stranded (ssDNA) more easily as they are heated at more high temperature, it is appropriate to be denatured at 94° C. in general because the activity of Taq. DNA Polymerase may be decreased at high temperature.

2) Primer Binding (Annealing)

The annealing process which binds the single stranded DNA with a primer, is, in general, proceeded 50° C. to 65° C. It can be possible to reduce the generation of non-specific product by means of raising the annealing temperature, particularly in case that non-specific product is serious.

3) DNA Replication (Polymerizaion, Extension)

The DNA replication is proceeded at 70° C. to 74° C. by the operation of Taq polymerase. In the case that the size of DNA to be amplified is large or the density of the cDNA is low, it is desirable to extend the replication time. The replication can be proceeded sufficiently by allowing a time of almost one (1) minute per 1 KB since Taq. Polymerase can replicate DNA of the length of 2,000 to 4,000 base pair per one (1) minute. The replication time should be prolonged gradually as replication is repeated, since the activity of Taq. Polymerase may be decreased, thus the replication time should be allowed sufficiently (10 minutes) in the final cycle to let the polymerase act thoroughly. The above processes are repeated (normally, 25 to 30 cycles) to amplify a desired part of DNA.

The Reverse Transcriptase-Polymerase Chain Reaction (RT-PCR), a similar reaction to the Polymerase Chain Reaction, is a process to amplify messenger ribonucleic acid (hereinafter, mRNA). This reaction is a process for replicating mRNA into complimentary DNA (cDNA) which then is amplified through the Polymerase Chain Reaction. This process is employed for searching a specific gene which cannot be detected from DNA, but can be detected only by RNA amplification.

Recently, the real-time Polymerase Chain Reaction has been known to the public. The real-time Polymerase Chain Reaction, is a technique which can monitor the process of the chain reaction in real-time, by means of measuring the intensity of the fluorescence emitted from reaction tube, which represents the progress of each cycle, without separation of the product of chain reaction on the gel. The real-time monitoring apparatus for this Polymerase Chain Reaction, is a machinery which is a combination of a thermal cycler for the Polymerase Chain Reaction and a fluorometer for detecting the reaction product. The conventional real-time monitoring apparatus for the Polymerase Chain Reaction, consists of a heat generator; thermal conduction block for heat transfer to a reaction tube containing reaction mixture; a light source to radiate light on reaction mixture in the tube; and a light receiving section for receiving fluorescence emitted from reaction mixture. The general scheme of real-time Polymerase Chain Reaction monitoring, comprises a step for repeating heating and cooling cycle by means of heat generator to proceed the reaction in a tube; a step for radiating light on the reaction mixture by using a light source at the end of the each cycle; and measuring the intensity of fluorescence emitted from the reaction mixture, to verify the progress of the Polymerase Chain Reaction.

However, the real-time monitoring apparatus for the Polymerase Chain Reaction which have been known to the public until now, have several problems that they cannot treat reaction mixture sequentially with a certain time interval whereas they can treat a large number of reaction mixture, and that other reaction mixture cannot be put into the apparatus until the reaction of the preceding mixture is completed. In addition, the conventional real-time monitoring apparatus should measure the intensity of fluorescence in each amplification cycle. Consequently, it provides a poor accuracy in measurement of the progress of the reaction, since measuring fluorescence of a number of reaction mixture takes a longer period of time.

Various real-time monitoring techniques of the Polymerase Chain Reaction have been studied and reported to overcome the problems of the conventional apparatus. The apparatus shown in FIG. 4 is similar to the apparatus of the present inventions amongst them.

FIG. 4 shows the Polymerase Chain Reaction machine based on the conventional technique (U.S. Pat. No. 6,033,880) which employs a capillary tube. The thermal conduction block (300) is composed of four (4) different types of constant temperature blocks (302, 303, 304, etc.). The reaction mixture and reagent are supplied into or removed from the capillary tube (351) by means of a reagent supplying apparatus (350). The thermal conduction rotates to change the temperature of the capillary tube and thus, the Polymerase Chain Reaction is performed. The common problems of this type of techniques are that it is required to rotate a thermal conduction block for the Polymerase Chain Reaction and that there may be a difference in the progress of the Polymerase Chain Reaction owing to the difference of contact between each capillary and thermal conduction block, which causes the decline of reproducibility.

In addition, it is unable to perform the Polymerase Chain Reaction continuously with a certain time interval in this type of apparatus. Moreover, there is a serious problem that it is unable to check the progress of reaction until the reaction is completed.

A novel apparatus for real-time monitoring of Polymerase Chain Reaction, which can overcome the problems of the conventional, has been introduced. J. H. Hahn et al. of Pohang University of Science and Technology proposed a temperature control and circulation apparatus for the continuous and stream-type Polymerase Chain Reaction which consists of a capillary and a round type thermal block (Korean Patent Application No. 10-2004-0006740, Feb. 4, 2004).

The above apparatus is composed of capillary tube in the length of 3.5 meters and coiled 33 rounds around the copper block of which a diameter is 30 millimeters, and which is made up of three temperature zones of melting, annealing and extension. Each cycle of PCR of the reaction mixture which flows within the capillary tube is proceeded upon each round around thermal block made from copper. (Nokyoung Park, Suhyeon Kim and Jong Hoon Hahn, Cylindrical Compact Thermal-Cycling Device for Continuous-Flow Polymerase Chain Reaction, Anal. Chem., 75, 6029-6033).

The process of Hahn et al. includes the step of coiling a heating block with capillary tube wherein the reaction mixture of Polymerase Chain Reaction flow; the step of radiating light on the capillary tube using a apparatus being located at a scanner; and the step of scanning the capillary tube using a scanning apparatus including a fluorometer to measure the intensity of the fluorescence generated from capillary tube.

In this process, a moving stage including a radiation part to radiate light on the capillary tube coiling around a heating block, and a sensor to measure the intensity of the fluorescence generated from the capillary tube moves the scanner linearly to radiate light on the capillary tube along with the path of the scanner, thus measuring the intensity of the fluorescence generated from the capillary tube.

The above patent of Hahn et al. describes a scanning apparatus which comprises a radiation part such as laser and lamp to generate light of a specific wavelength; and a fluorescence detector such as PMT and diode, wherein said radiation part and said fluorescence detector move as a constant speed on the heating block which is coiled with a capillary tube for scanning. A scanner having the radiation part and fluorescence detection sensors attached thereto moves along the axis which is parallel or perpendicular to the axis of the heating block coiled with a capillary tube, thus radiating light on the capillary tube or measuring the intensity of the fluorescence.

It is necessary to have a transporting apparatus such as a stepping motor and a linear transporting means, a guidance apparatus for transporting, and a driving means to provide power to a transporting apparatus, in order to have a portion for the fluorescence detection part and a fluorometer attached to a moving stage and move the moving stage at a constant speed, scanning and detecting the generated fluorescence continuously. The radiation and radiation part which uses one or more optical lenses should use not only the highly costed optical lenses such as substance lens, but also a delicate arrangement apparatus for precise adjustment and deviation of the light channel. These optical apparatuses which are used for radiation and to control and adjust the light channel are not only expensive but also take considerable space. Moreover, these driving means, power transmission means, transporting apparatus, and etc. also cause the problem of the space required for an apparatus for the Polymerase Chain Reaction, because these mechanical apparatuses and linear motor apparatuses make the Polymerase Chain Reaction machine large in size and may cause frequent breakdown and malfunction.

As considered above, one or more expensive lenses including a substance lens should be used to radiate light on the capillary tube that changes its location according to the movement of light source. Another cause of raising the production cost of the Polymerase Chain Reaction machine is the delicate mechanical processing on installation.

The apparatus of Hahn et al. monitors the Polymerase Chain Reaction whenever the scanner having a moving light source, a fluorescence detection part and one or more expensive optical lens apparatuses attached thereto scans one or more capillary tubes.

Such scanning method causes problems such as that light may be radiated during the scanning process, that it can only monitor the reaction within the capillary tube when the fluorometer passes and that it cannot monitor the reaction that occurs at the other part within the capillary tube where the scanner cannot cover.

Therefore, there is a need in the art to develop a new type of the real-time monitoring apparatus to overcome the chronic problems in Hahn et al. by providing a smaller in size, inexpensive, continuously performing, practical and effective real-time monitoring apparatus.

DISCLOSURE OF INVENTION

Technical Problem

Therefore, the purpose of the present invention is to provide a new type of apparatus for real-time monitoring of Polymerase Chain Reaction as a monitoring apparatus to verify the progress of the reaction during the continuous reaction of the chemical mixture, which is extremely miniaturized, inexpensive, and has low possibility of breakdown or malfunction.

More particularly, the present invention is directed to a miniaturized apparatus for real-time monitoring of biochemical reaction, which comprises capillary tubes (100) wherein the biochemical reaction mixture flow; a thermal conduction block (120) which is coiled with capillary tube several rounds in order and composed of several blocks for temperature control of which temperatures are different from each other for heating or cooling the biochemical reaction mixture which flow in capillary tube, and a temperature controller which controls the temperature of above temperature control block; a radiation part (130) to radiate the reaction mixture flowing through the capillary tube and a light receiving section (140) which receives and measures the intensity of the fluorescence generated from the capillary tubes. And the purpose of the present invention is to provide a apparatus for continuous real-time monitoring of Polymerase Chain Reaction, which radiates light on many capillary tubes at the same time by using the light beam whose section is linear to radiate light on the above capillary tubes, and wherein a sensor to detect the generated fluorescence is arranged along the same axis of a heating block Furthermore, the purpose of the present invention is to provide a apparatus for continuous real-time monitoring of Polymerase Chain Reaction which can measure the progress of the reaction of the various reagents by separating one reaction mixture from another and passing it sequentially through capillary tube, while monitoring the progress of the continuous reaction of various reagents.

Technical Solution

The inventors of the present invention completed the invention based on the fact that it is possible to embody the apparatus for continuous real-time monitoring of Polymerase Chain Reaction which is miniaturized, low-priced, and has low possibility of breakdown by devising a new scheme whereby light is continuously radiated on the reagent and the intensity of the generated fluorescence is continuously measured, whereas in the prior technique light is radiated on the reagent flowing through capillary tubes periodically and the intensity of the generated fluorescence is measured periodically.

The present invention provides the apparatus for a real-time monitoring of the Reverse Transcription-Polymerase Chain Reaction, wherein the reaction mixture is passed to a reaction mixture pretreatment block (180) before it is amplified a thermal conduction block (120). The real-time monitoring of the Reverse Transcription-Polymerase Chain Reaction may be processed by adding the reaction mixture of reverse transcriptase to the reaction reagent (151) and making the above reaction mixture reacted within a reaction mixture pretreatment block (180) at a constant temperature (generally 42° C.) for a certain period of time. When the apparatus of the present invention is not used for monitoring of the Reverse Transcription-Polymerase Chain Reaction, the temperature of the pretreatment block (180) is adjusted to be same as that of a heating block (170).

More particularly, the present invention provides an apparatus for continuous realtime monitoring of biochemical reaction, which comprises, a thermal conduction block (120) which is coiled with capillary tube several rounds in order and composed of several blocks for temperature control of which temperatures are different from each other for heating or cooling the biochemical reaction mixture which flow in capillary tube; capillary tubes (100) coiled around said thermal conduction block (120), wherein the biochemical reaction mixture flow; a temperature controller which controls the temperature control block; a radiation part (130) to radiate the reaction mixture flowing through the capillary tube; and a light receiving section (140) which comprises linear array detector which measure the intensity of the fluorescence generated from the capillary tubes.

The technical characteristic of the present invention is that a radiation part (130) uses Linear-Facet light from Linear-Facet Light Source or changed from light of the general light source. The apparatus of the present invention uses Linear-Facet light of which section is a long and linear type rather than a circle as in the prior techniques, thus radiating linear lights at the same time in the parallel direction to the axis of the long cylindrical thermal conduction block on the whole capillary tubes coiling compactly around the thermal conduction block at the same time. If the length of linear light is adjusted to be equal to the size of the cylindrical thermal conduction block which is compactly coiled with capillary tubes, it is not necessary to set a scanner on a radiation part and move the part around the capillary tubes, as it is able to radiate light on the whole capillary tubes with one linear light. That is, the apparatus of the present invention is technically characterized in that the whole capillary tubes can be radiated at the same time with the identical light, by adjusting the length of linear light to the size of the thermal conduction block which is coiled with capillary tubes.

Another characteristic of the apparatus in the present invention is that a fluorescence detector uses a linear array detector which comprises a linear type supporter where numerous detection sensors are arranged, as in a linear charge coupled device (CCD). The fluorescence generated from each capillary tube can be detected at the same time without using the scanner which requires the fluorescence detection sensor to be adapted in the scanner, by adjusting the length of the linear array sensor to the size of the cylindrical thermal conduction block which is compactly coiled with capillary tubes, then by arranging and fixing the above linear array sensor along the axis parallel to the central axis of the thermal conduction block.

According to the present invention, the Polymerase Chain Reaction can be processed for the reaction of the biological reaction mixture, as described in the FIG. 1, by pushing the above reaction reagent and reaction mixture into the capillary tube with a certain time interval by using a metering pump after coiling the thermal conduction block (120) several rounds with capillary tube, then by flowing the above reaction mixture through the capillary tube in one direction and passing the above reaction mixture several times repeatedly between two temperature blocks (121, 122) which are different from each other. That is, the Polymerase Chain Reaction is processed, whenever the reaction mixture within the capillary tube circulates once through the capillary tube coiling around the thermal conduction block (120).

Since the capillary tube is coiled around the thermal conduction block many times, the reaction cycle becomes longer in proportion to the number of coiling. A reactionary error caused by difference in heat conduction will not occur, because the capillary tube itself will not move due to the fact that the thermal conduction block (120) is coiled with capillary tubes.

Furthermore, in the apparatus of the present invention, the Polymerase Chain Reaction begins after heating the reaction mixture in 94° C. for several minutes to make the reaction progresses smoothly and it is not necessary to set up a heating block (170) separately, thus processing the reaction automatically without the human intervention, also the reaction mixture pretreatment block (180) is set for the special reaction such as Reverse-Transcription prior to the thermal conduction block (120), thus processing the Reverse-Transcription separately from the Polymerase Chain Reaction.

In the present invention, each elapsed time for the reaction in a heating block (170) and a reaction mixture pretreatment block (180) is decided by the number of rounds of the capillary tube coiling around each block and by the size of each block.

In addition, in the present invention, it is possible to quantitatively measure the progress of the Polymerase Chain Reaction in a real-time, through measuring the intensity of the fluorescence generated from the reaction mixture which sequentially reacts, simultaneously at the moment of the reaction, by providing the radiation part (130) and the light receiving section (140).

The present invention provides a process for monitoring multiple biochemical reactions in a single capillary tube quantitatively with a certain time interval, which comprises, a step for supplying reaction mixtures sequentially with a certain time interval into capillary tube of apparatus for continuous real-time monitoring of biochemical reaction, which comprises, a thermal conduction block (120) composed of several blocks for temperature control of which temperatures are different from each other for heating or cooling the biochemical reaction mixtures which flow in a capillary tube; capillary tubes (100) coiled around said thermal conduction block (120), wherein the biochemical reaction mixtures flow; a temperature controller which controls the temperature control blocks; a radiation part (130) to radiate the reaction mixtures flowing through the capillary tube; and a light receiving section (140) which comprises linear array detector which measures the intensity of the fluorescence generated from the capillary tubes;

a step for proceeding a reaction by changing the temperature of the mixtures by passing the mixtures through the capillary tube coiling around the thermal conduction block; and a step for measuring fluorescence generated from reaction mixtures within the capillary tubes.

The present invention further provides a process for monitoring concurrently each cycle of biochemical reaction in a single capillary tube, which comprises, a step for supplying a reaction mixture automatically with a certain amount into capillary tube of the apparatus for continuous real-time monitoring of biochemical reaction, which comprises, a thermal conduction block (120) composed of several blocks for temperature control of which temperatures are different from each other for heating or cooling the biochemical reaction mixture which flow in capillary tube; capillary tubes (100) coiled around said thermal conduction block (120), wherein the biochemical reaction mixture flow; a temperature controller which controls the temperature control blocks; a radiation part (130) to radiate the reaction mixture flowing through the capillary tube; and a light receiving section (140) which comprises linear array detector which measure the intensity of the fluorescence generated from the capillary tubes;

a step for proceeding a reaction by changing the temperature of the said reaction mixture by passing the said reaction mixture through the capillary tube coiling around the thermal conducting block (120); and a step for measuring concurrently each reaction cycle from the numerous capillary tubes.

Advantageous Effects

In the apparatus of the present invention, the progress of reaction can be measured per each cycle, by measuring the intensity of fluorescence generated from each capillary tube after the reaction mixture was sequentially flowed through the capillary tube with a certain time interval.

The present invention is related to the apparatus which can be effectively used in the fields (e.g. detecting the pathogenic microorganisms in the air, monitoring the water pollution, detection and identification of the biological terror, and others) which require continuous collection and measurement of the reaction mixture with a certain time interval. This apparatus can be effectively used in the above industrial fields as the conventional technique which cannot process the reaction of reaction mixture with a certain time interval was dramatically improved.

In addition, the apparatus of the present invention can greatly minimize the elapsed time for the reaction, as only small amount of reaction mixture flows within the capillary tube, and the above apparatus can increase the reproducibility and stabilization of the reaction by improving the problem of the conventional apparatus that there can be difference in conducting of heat due to the space between the thermal conduction block and a reaction vessel, by coiling the capillary tube in order around the thermal conduction block (120).

In addition, in the reactivity can be improved and the special reaction such as pre-treatment reaction can be realized, by adapting a heating block (170) and reaction mixture pretreatment block (180) separately, and also it is possible to measure the progress of the reaction of numerous reaction mixtures and many reaction cycles at once, by concurrently measuring the intensity of the fluorescence generated from numerous capillary tubes with the linear type of sensor.

In addition, in the case that numerous reaction mixtures are measured concurrently in the apparatus of the present invention, it is possible to measure the progress of the reaction for each reaction mixture by sequentially flowing the above reaction mixtures through the capillary tube separately.

BRIEF DESCRIPTION OF THE DRAWINGS

FIG. 1 is an overall schematic diagram of the apparatus for quantitative continuous real-time monitoring of the present invention.

FIG. 2 is a detail drawing(front figure and plane figure) related with a thermal conduction block of the apparatus for quantitative continuous real-time monitoring of the present invention.

FIG. 3 is a detail drawing related with a radiation part and a light receiving section identified in FIG. 1 in the detail drawing of the apparatus for quantitative continuous real-time monitoring of the present invention.

FIG. 4 is a drawing showing the PCR (Polymerase Chain Reaction) apparatus which is using many capillary tubes and constituted by the conventional technique.

FIG. 5 is a graph which shows the quantity of the fluorescence of the reaction mixture for each reaction cycle after finishing the reaction which was performed several times with one kind of reaction mixture.

FIG. 6 to FIG. 8 are graphs which shows the quantity of the fluorescence of each reaction mixture in each cycle of each reaction mixture, while numerous reaction mixture is reacting at the same time.

BRIEF DESCRIPTION OF MAIN PARTS OF THE DRAWINGS

160: multiplex channel valve,
110, 111, 112, 113, 114: quantitative pump,
120: thermal conduction block,
121: denaturation block,
122: annealing block,
123, 125, 171, 181: pipe heater,
124, 126, 172, 182: temperature controller,
127: insulating material,
140: light receiving section,
130: radiation part,
170: heating block,
151: reaction reagent,
152: mineral oil,
153: distilled water,
154: detergent,
155: reaction mixture reaction plate,
156: wastewater bottle,
180: pretreatment block
143: light receiving sensor,
141: fluorescence reception lens,
100: bundle of capillary tubes,
131: excitation transmitting lens,
132, 142: band pass filter,
133: LED array board Best Mode for Carrying out the Invention The examples below are provided to illustrate the subject with drawings, but not to limit the present invention.

The present invention is an apparatus for the real-time quantitative monitoring of the reaction of biochemical reaction mixture, which comprises, as shown in FIG. 1, a storage vessel (151 to 154) where reaction mixture, capillary tube detergent, and solution for a reaction are contained, a storage vessel (155) containing the reaction mixture to be analyzed, a quantitative pump (110 to 114) to transfer the reaction mixture, a multiplex channel valve (160) which repeatedly transfers various solutions to capillary tube in order, a thermal conduction block (120) comprises the plural number of temperature control blocks of which temperatures are different from each other for heating or cooling the biochemical reaction mixture, a radiation part (130) to radiate the excitation light to generate fluorescence from a reaction mixture, a light receiving section (140) to measure the intensity of the fluorescence generated from a reaction mixture at the same time, a heating block (170) to heat for the pretreatment of a reaction mixture, a pretreatment block (180) to selectively pretreat reaction mixture, a wastewater bottle (156) where the reaction mixture of the completed reaction is discharged.

A thermal conduction block is composed of separated temperature blocks which respectively maintain various temperatures, and each block form a circular pole by combining with each other by using insulating material (127). In the present invention, a denaturation block which is maintained from 90° C. to 94° C., specially in 94° C., and an annealing block (122) which is maintained from 50° C. to 65° C., specially in 55° C. are constituted, as the most typical example, and temperature of each block can be controlled according to the state of the reaction mixture and experimental condition by using a temperature controller (124, 126) and a pipe heater (123, 125).

The individual block can be adapted more according to the state of reaction mixture and the experimental condition, for example, an extension block which is maintained from 70° C. to 75° C. can be adapted more. In addition, each individual block combines with each other by using insulating material (127), and form a circular form like a thermal conduction block (120).

FIG. 3 illustrates a radiation part and a light receiving section more in detail. The LED array board (133) is arrayed to generate energy for generating fluorescence from the above reaction mixture within the capillary tube, and the excitation light from the above LED array board passes the band pass filter (132) which selectively passes light with a specific wavelength and changes it to monochromatic light, then said monochromatic light is condensed through a excitation transmitting lens (131) and inputted into capillary tubes (100).

The reaction mixture in the capillary tube gains energy and radiate fluorescence, and the said fluorescence is condensed to a fluorescence reception lens (141) to effectively transmit the fluorescence to a sensor, thereby the excitation light is eliminated and the fluorescence only passes a band pass filter (142) which selectively passes fluorescence, then the above fluorescence is inputted into a light receiving sensor wherein intensity of fluorescence is measured. In the above process, a light receiving sensor has a linear form and uses photodiode array or linear charge coupled device (CCD).

Mode for the Invention

The constitution and the function of the present invention are illustrated more concretely by the following examples.

EXAMPLE 1

In the case that the Polymerase Chain Reaction was performed through the present invention, the constitutional and the functional scheme which enables simultaneously all the every progress of each cycle for one kind of reaction mixture, not by measuring per every cycle, when the reaction is completed, comprises the following steps.

At first, the detergent (154) is transferred within the capillary tube to wash capillary tube by using a quantitative pump (113); then the quantitative pump (112) connected to distilled water (153) for washing was operated to push distilled water within the capillary tube until the distilled water reached the wastewater bottle (156); thereby the process to wash the inside of the capillary tube was completed.

Then, constant quantity of the reaction reagent (151) and the reaction mixture (155) was inputted within the capillary tube by using the quantitative pumps (110 and 114) alternately. In this progress, the above quantity was limited according to the number of bundle of capillary tubes, thereby a light receiving sensor of light receiving section (140) can detect among the capillary tubes coiling around a thermal conduction block (120). After the above process, mineral oil (152) was continuously inputted into the capillary tube by using a quantitative pump (111), then the previously inputted reaction mixture and reagent circulated between the denaturation block (121) and the annealing block (122) of the thermal conduction block (120), thereby the Polymerase Chain Reaction was performed. In the case that the previously inputted reaction mixture continuously circulated through the thermal conduction block (120) and reached right in front of the wastewater bottle, then the reaction came to an end.

FIG. 2 is the front figure and the plane figure of the thermal conduction block (120). In the left front figure, in the case that the Polymerase Chain Reaction was performed N cycles within the lowest capillary tube, it means that the Polymerase Chain Reaction within the capillary tube which is just above the said capillary tube was performed N-1 cycles. Therefore, the fluorescence of each cycle, as N, N-1, N-2, N-3, and more cycles could be measured at the same time, in the case that the intensity of fluorescence was measured by using a light receiving sensor (143).

FIG. 5 shows the pattern for the increase of intensity of fluorescence for the example 1. The shape of the graph could be changed by the state of the reaction mixture and the concentration of the reaction mixture. The fluorescence was detected weakly after the 15th reaction cycle. Though the intensity of fluorescence had to increase $2^n$ times per every cycle in theory, however the intensity of fluorescence actually increased $1.7^n$ times. In addition, the intensity of fluorescence did not continuously increase $1.7^n$ times per each cycle, and in the case that the reaction reached a certain cycle, the intensity of fluorescence did not increase anymore due to the limitation of the reaction reagent and the quantity of fluorescence became saturated. For example, in accordance with the FIG. 5, in the case that the reaction reached the 30th cycle, the quantity of fluorescence became saturated and the intensity of fluorescence did not increased anymore.

EXAMPLE 2

The following is the constitutional and functional scheme of the present invention to measure numerous reaction mixtures continuously with a certain time interval.

The process to wash capillary tube was same as example 1. After washing, the certain quantity of reaction reagent (151) and reaction mixture (155) was inputted within the capillary tube by operating the quantitative pump (110 and 114) alternatively. During the above process, The scope of quantity of the inputted reaction reagent and reaction mixture should be above the scope wherein the above reaction reagent and reaction mixture can be detected by the light receiving section (140), and should be under the scope of a certain amount for one (1) cycle of the capillary tube coiling around the thermal conduction block (120). The rest part of total amount of the reaction mixture was filled with mineral oil (152), thereby the amount for one (1) reaction cycle was prepared and then inputted within the capillary tube coiling around the thermal conduction block (120), then other reaction mixtures were sequentially inputted within the capillary tube as the above process.

In the real-time Polymerase Chain reaction, the fluorescence could be detected after the 15th cycle in general. Therefore, the light receiving sensor is not required to detect the whole capillary tubes coiling around the thermal conduction block (120), and required to detect capillary tubes after the 15th cycle. In this example, capillary tube coiled 40 rounds in total, however, the light receiving sensor detected the 15th to the 40th cycle.

The Polymerase Chain Reaction was performed, as the reaction mixture filled within the capillary tube flowed through the capillary tube coiling around the thermal conduction block (120). In the above process, the quantitative detection data related to the 15th to 40th cycle of the Polymerase Chain Reaction can be sequentially collected, by detecting the fluorescence of 40 reaction mixtures through the sensor of the light receiving section (142).

FIG. 6 to FIG. 8 show the pattern of the increase of fluorescence for the example 2. In the case that fluorescence was detected after the 15th reaction cycle, the reaction mixture firstly inputted only generated the fluorescence. In the graph after the 19th reaction cycle, the fluorescence of the reaction mixture firstly inputted was detected most strongly in the capillary tube number 19. That is, the above reaction mixture originally was the reaction mixture of the capillary tube number 15 in the graph of the 15th reaction cycle, then was detected in the 19th capillary tube after 4 more reaction cycles were processed. In the same Figure, the capillary tube number 18 contains the secondly inputted reaction mixture, the capillary tube number 17 contains the thirdly inputted reaction mixture, and the capillary tube number 15 contains the fifthly inputted reaction mixture. The last graph shows the intensity of fluorescence after the 30th Polymerase Chain Reaction was processed.

The firstly inputted reaction mixture was detected in the 30th capillary tube, and the quantity of fluorescence generated from the above capillary tube became saturated. The intensity of fluorescence for 16 reaction mixtures from the 15th capillary tube to the 40th capillary tube could be obtained at the same time.

Industrial Applicability

The continuous and quantitative reaction apparatus of the present invention is suitable to be used in PCR reaction, sequencing reaction, and real-time PCR reaction.

Sequence Listing
   NO.

The invention claimed is:

1. An apparatus for continuous real-time monitoring of biochemical reaction, which comprises:
   a thermal conduction block composed of several blocks for temperature control of which temperatures are different from each other for heating or cooling the biochemical reaction mixture which flow in capillary tube;
   capillary tubes coiled around said thermal conduction block, wherein the biochemical reaction mixture flow;
   a temperature controller which controls the temperature control block;
   a radiation part comprising an excitation transmitting lens, a band-pass filter and a light source to radiate a light beam whose section is linear to the reaction mixture flowing through the capillary tube; and
   a light receiving section which comprises linear array detector which measures the intensity of the fluorescence generated from the capillary tubes,
   wherein the radiation part and the light receiving section are arranged along the same axis of the thermal conduction block, and
   the radiation part and the light receiving section are positioned oppositely around the capillary tubes.

2. The apparatus according to claim 1, which further comprises a pretreatment block for a progress of pretreatment reaction of reaction mixture before said biochemical reaction mixture reaches the thermal conduction block.

3. The apparatus according to claim 1, which further comprises a heating block for heating the reaction mixture before said reaction mixture reaches the thermal conduction block.

4. The apparatus according to claim 1, wherein said thermal conduction block is composed of two thermal blocks of denaturation block and annealing block, and an insulating material which combines each thermal blocks.

5. The apparatus according to claim 1, wherein said thermal conduction block is composed of three thermal blocks comprising a denaturation block, an annealing block and an extension block.

6. The apparatus according to claim 1, wherein said capillary tubes are coiled 10 coils to 45 coils around the thermal conducting block.

7. The apparatus according to claim 2 or claim 3, wherein the reaction time in each block is controlled according to the size of heating block and pretreatment block, and according to a number of coils of the capillary tube coiling around each blocks.

8. The apparatus according to claim 1, which further comprises a multi-channel valve which transmits various biochemical mixture sequentially through the capillary tubes.

9. The apparatus according to claim 1, wherein said light receiving section comprises linear charge coupled device (CCD) to detect concurrently the fluorescence generated from the numbers of capillary tubes, which corresponds to a number of occurrences of a reaction cycle.

10. The apparatus according to claim 1, wherein said light receiving section comprises linear photo diode array to detect concurrently the fluorescence generated from the numbers of capillary tubes, which corresponds to a number of occurrences of a reaction cycle.

* * * * *